(12) United States Patent
Bishop et al.

(10) Patent No.: US 10,610,421 B2
(45) Date of Patent: Apr. 7, 2020

(54) ABSORBENT ARTICLE WITH POCKET AND SECONDARY FASTENING SYSTEM

(71) Applicant: Kimberly-Clark Worldwide, Inc, Neenah, WI (US)

(72) Inventors: David F. Bishop, Appleton, WI (US); Sara Stabelfeldt, Appleton, WI (US); Nicole J. Barna, Appleton, WI (US); Nancy E Dawson, Appleton, WI (US); Jeffrey A DeBroux, Appleton, WI (US); John T. Hahn, Merrill, WI (US); Eric D. Johnson, Neenah, WI (US); Georgia L. Zehner, Larsen, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 423 days.

(21) Appl. No.: 15/511,098

(22) PCT Filed: Sep. 30, 2014

(86) PCT No.: PCT/US2014/058208
§ 371 (c)(1),
(2) Date: Mar. 14, 2017

(87) PCT Pub. No.: WO2016/053275
PCT Pub. Date: Apr. 7, 2016

(65) Prior Publication Data
US 2017/0246050 A1 Aug. 31, 2017

(51) Int. Cl.
*A61F 13/56* (2006.01)
*A61F 13/49* (2006.01)
(Continued)

(52) U.S. Cl.
CPC ........ *A61F 13/49058* (2013.01); *A61F 13/49* (2013.01); *A61F 13/496* (2013.01);
(Continued)

(58) Field of Classification Search
CPC .............. A61F 13/5622; A61F 13/5644; A61F 13/565; A61F 13/581; A61F 13/622;
(Continued)

(56) References Cited

U.S. PATENT DOCUMENTS

| 3,865,110 A | 2/1975 | Traverse |
| 5,308,345 A | 5/1994 | Herrin |

(Continued)

FOREIGN PATENT DOCUMENTS

| EP | 1 688 117 A1 | 8/2006 |
| GB | 2298354 A1 | 9/1996 |

(Continued)

*Primary Examiner* — Catharine L Anderson
(74) *Attorney, Agent, or Firm* — Kimberly-Clark Worldwide, Inc.

(57) ABSTRACT

An absorbent article (10) can include a fastening system including a primary fastening system (82) and a secondary fastening system (84). The primary fastening system (82) can include at least one primary first fastening component (86) and at least one primary second fastening component (88). The secondary fastening system (84) can include a first secondary first fastening component (96) and at least one secondary second fastening component (98). The absorbent article (10) can also include a pocket (64) disposed in the front waist region (12) such that at least one primary first fastening component (86) is configured to engage the pocket (64) when engaging the at least one primary second fastening component (88) in the fastened condition of the absorbent article (10) and the first secondary first fastening component (96) can engage the at least one secondary second fastening component (98) in the fastened condition.

17 Claims, 7 Drawing Sheets

(51) Int. Cl.
  *A61F 13/496* (2006.01)
  *A61F 13/62* (2006.01)

(52) U.S. Cl.
  CPC ............ *A61F 13/56* (2013.01); *A61F 13/565* (2013.01); *A61F 13/5633* (2013.01); *A61F 13/5644* (2013.01); *A61F 13/622* (2013.01)

(58) Field of Classification Search
  CPC .................. A61F 13/625; A61F 13/627; A61F 2013/49098; A61F 2013/55125; A61F 2013/5683; A61F 13/5519
  See application file for complete search history.

(56) References Cited

U.S. PATENT DOCUMENTS

| | | | |
|---|---|---|---|
| 5,593,401 | A * | 1/1997 | Sosalla ............. A61F 13/49011 604/385.28 |
| 5,778,110 | A | 7/1998 | Furuya |
| 5,904,675 | A | 5/1999 | Laux et al. |
| 5,938,652 | A | 8/1999 | Sauer |
| 6,258,076 | B1 | 7/2001 | Glaug et al. |
| 6,264,639 | B1 | 7/2001 | Sauer |
| 6,425,889 | B1 | 7/2002 | Kitaoka et al. |
| 6,485,478 | B2 * | 11/2002 | Imai .................... A61F 13/5633 604/385.01 |
| 7,727,211 | B2 | 6/2010 | Beck |
| 7,982,090 | B2 | 7/2011 | Snauwaert et al. |
| 7,993,314 | B2 | 8/2011 | Asp et al. |
| 2001/0037102 | A1 | 11/2001 | Sugito |
| 2003/0109841 | A1 | 6/2003 | Edwards |
| 2005/0137564 | A1 | 6/2005 | Strannemalm |
| 2005/0143710 | A1 | 6/2005 | Van Gompel et al. |
| 2006/0111685 | A1 | 5/2006 | Kawata et al. |
| 2006/0241558 | A1 | 10/2006 | Ramshak |
| 2006/0282056 | A1 | 12/2006 | McDonald |
| 2007/0032769 | A1 | 2/2007 | Cohen et al. |
| 2008/0051744 | A1 | 2/2008 | Cummings |
| 2011/0034896 | A1 | 2/2011 | Bai |
| 2011/0092939 | A1 | 4/2011 | Donoho |
| 2012/0071850 | A1 | 3/2012 | Tomassetti |

FOREIGN PATENT DOCUMENTS

| | | |
|---|---|---|
| GB | 2 326 811 A | 1/1999 |
| GB | 2 389 300 A | 12/2003 |
| WO | WO 1998/013002 A1 | 4/1998 |

* cited by examiner

ABSORBENT ARTICLE WITH POCKET AND SECONDARY FASTENING SYSTEM

TECHNICAL FIELD

The present invention relates to absorbent articles.

BACKGROUND OF THE DISCLOSURE

When absorbent articles become soiled with exudates and are changed from the wearer, it is common for the lower abdomen and/or crotch region of the wearer to become soiled by urine, fecal matter, and/or other bodily discharges. Prior to replacing the soiled absorbent article and replacing it with a new, clean absorbent article, the skin of the wearer is cleansed. This cleaning of the skin can be done in a variety of ways and using a variety of different materials, but caregivers commonly use wet wipes or cloths to cleanse the wearer's skin. In some circumstances, caregivers may choose to use a clean portion of an inner layer of the soiled absorbent article to provide a first wipe to cleanse the wearer's skin in the lower abdomen or crotch region prior to using wet wipes, cloths, or tissues.

To perform this initial wipe, a caregiver may attempt to pinch or gather the front waist region of the absorbent article to obtain a grip on the absorbent article to use the inner layer of the absorbent article in a wiping fashion. However, pinching or gathering the front waist region of the absorbent article can reduce the effective area of the inner layer of the absorbent article that is intended to wipe the wearer's skin in the soiled area as well as create an uneven inner surface of the absorbent article that is not as conducive to wiping as the initial flat surface. Pinching or gathering the front waist region of the absorbent articles in this fashion may also expose a caregiver's fingers or hand to the exudates remaining on the wearer's skin, as the gathered material in the front waist region may fold over due to pinching or gathering of the absorbent article near the front waist edge of the absorbent article where the absorbent article may have less structural integrity and/or due to the wiping motion of the caregiver employs with the absorbent article. Additionally, gripping the front waist region of the absorbent article in such a fashion may prove to be difficult altogether as the outer cover materials may have a low coefficient of friction, resulting in the gathered or pinched area of the front waist region slipping out of the caregiver's hands while trying to wipe the soiled area.

A prior document has attempted to address these issues by the introduction of a pocket in the front waist region of the absorbent article to assist with cleaning the wearer. GB 2389300A discloses various embodiments of absorbent articles including such a pocket. However, absorbent articles including a pocket in the front waist region may suffer from poor fit from the fastening system where the fasteners engage material forming the pocket or material that is directly coupled to the material forming the pocket due to the fact these materials can move with respect to the rest of the absorbent assembly. As a result, the fastening system in such embodiments may loosen from the original desired tension applied to the fastening system by the caregiver, resulting in reduced fit characteristics during wear and/or increased likelihood of the gaskets of the absorbent article failing.

Thus, there remains a need for an absorbent article that can provide improved functionality for the caregiver to utilize the absorbent article as a first wipe to cleanse the wearer's skin, yet still retain proper fit maintenance of the fastening system of the absorbent article.

SUMMARY OF THE DISCLOSURE

In one embodiment, an absorbent article can include a front waist region including a front waist edge, a rear waist region including a rear waist edge, and a crotch region. The absorbent article can further include a longitudinal axis and a lateral axis. The longitudinal axis can provide a first longitudinal half of the absorbent article and a second longitudinal half of the absorbent article. The absorbent article can be configured to move between an unfastened condition and a fastened condition. The absorbent article can include an absorbent assembly including a bodyside liner, an outer cover, and an absorbent body disposed between the bodyside liner and the outer cover. The absorbent article can further include a fastening system including a primary fastening system and a secondary fastening system. The primary fastening system can include at least one primary first fastening component in the rear waist region and at least one primary second fastening component in the front waist region. The secondary fastening system can include a first secondary first fastening component in the front waist region and at least one secondary second fastening component in the rear waist region. The first secondary first fastening component can include a first inner longitudinal edge and a first outer longitudinal edge. The absorbent article can also include a pocket including a first side edge, a second side edge opposite from the first side edge, an upper lateral edge, and a lower lateral edge. The pocket can be closed with respect to the absorbent assembly at least at the first side edge and the second side edge and can be open with respect to the absorbent assembly at least at the lower lateral edge. The pocket can be disposed in the front waist region such that the at least one primary first fastening component is configured to engage the pocket when engaging the at least one primary second fastening component in the fastened condition of the absorbent article and the first secondary first fastening component engaging the at least one secondary second fastening component in the fastened condition.

In another embodiment, an absorbent article can include a front waist region including a front waist edge, a rear waist region including a rear waist edge, and a crotch region. The absorbent article can further include a longitudinal axis and a lateral axis. The longitudinal axis can provide a first longitudinal half of the absorbent article and a second longitudinal half of the absorbent article. The absorbent article can also include an absorbent assembly including a bodyside liner, an outer cover, and an absorbent body disposed between the bodyside liner and the outer cover. The absorbent article can further include a pocket disposed in the front waist region. The pocket can include a first side edge, a second side edge opposite from the first side edge, an upper lateral edge, and a lower lateral edge. The pocket can be closed with respect to the absorbent assembly at least at the first side edge and the second side edge and can be open with respect to the absorbent assembly at least at the lower lateral edge. The absorbent article can also include a fastening system including a primary fastening system and a secondary fastening system. The primary fastening system can include at least one primary first fastening component in the rear waist region and at least one primary second fastening component in the front waist region. The secondary fastening system can include a first secondary first fastening component in the front waist region and at least one secondary second fastening component in the rear waist region.

The first secondary first fastening component can be disposed in the first longitudinal half of the absorbent article. The first secondary first fastening component can include a first inner longitudinal edge. At least a portion of the first inner longitudinal edge can be laterally outside of the first side edge of the pocket.

In yet another embodiment, an absorbent article can include a front waist region including a front waist edge, a rear waist region including a rear waist edge, and a crotch region. The absorbent article can further include a longitudinal axis and a lateral axis. The longitudinal axis can provide a first longitudinal half of the absorbent article and a second longitudinal half of the absorbent article. The absorbent article can also include an absorbent assembly including a bodyside liner, an outer cover, and an absorbent body disposed between the bodyside liner and the outer cover. The absorbent article can further include a pocket disposed in the front waist region. The pocket can include a first side edge, a second side edge opposite from the first side edge, an upper lateral edge, and a lower lateral edge. The pocket can be closed with respect to the absorbent assembly at least at the first side edge and the second side edge and can be open with respect to the absorbent assembly at least at the lower lateral edge. The absorbent article can further include a fastening system including a primary fastening system and a secondary fastening system. The primary fastening system can include at least one primary first fastening component in the rear waist region and at least one primary second fastening component in the front waist region. The secondary fastening system can include a first secondary first fastening component in the front waist region and at least one secondary second fastening component in the rear waist region. The first secondary first fastening component can be disposed in the first longitudinal half of the absorbent article. The first secondary first fastening component can include a first inner longitudinal edge, a first outer longitudinal edge and a first area. A majority of the first area can be outside of the pocket.

In still another embodiment, an absorbent article can include a front waist region including a front waist edge, a rear waist region including a rear waist edge, and a crotch region. The absorbent article can further include a longitudinal axis and a lateral axis. The longitudinal axis can provide a first longitudinal half of the absorbent article and a second longitudinal half of the absorbent article. The absorbent article can include an absorbent assembly including a bodyside liner, an outer cover, and an absorbent body disposed between the bodyside liner and the outer cover. The absorbent assembly can further include a first longitudinal edge and a second longitudinal edge, the first longitudinal edge connecting the front waist edge and the rear waist edge and being disposed in the first longitudinal half of the absorbent article. The second longitudinal edge can connect the front waist edge and the rear waist edge and can be disposed in the second longitudinal half of the absorbent article. The absorbent article can further include a pocket disposed in the front waist region. The pocket can include a first side edge, a second side edge opposite from the first side edge, an upper lateral edge, and a lower lateral edge. The pocket can be closed with respect to the absorbent assembly at least at the first side edge and the second side edge and can be open with respect to the absorbent assembly at least at the lower lateral edge. The absorbent article can further include a fastening system including a primary fastening system and a secondary fastening system. The primary fastening system can include at least one primary first fastening component in the rear waist region and at least one primary second fastening component in the front waist region. The secondary fastening system can include a first secondary first fastening component in the front waist region and at least one secondary second fastening component in the rear waist region. The first secondary first fastening component can be disposed in the first longitudinal half of the absorbent article and can include a first inner longitudinal edge and a first outer longitudinal edge. The first inner longitudinal edge of the first secondary first fastening component can be laterally closer to the first longitudinal edge of the absorbent assembly than the first side edge of the pocket is to the first longitudinal edge of the absorbent assembly.

BRIEF DESCRIPTION OF DRAWINGS

A full and enabling disclosure thereof, directed to one of ordinary skill in the art, is set forth more particularly in the remainder of the specification, which makes reference to the appended figures in which.

Figure 1:
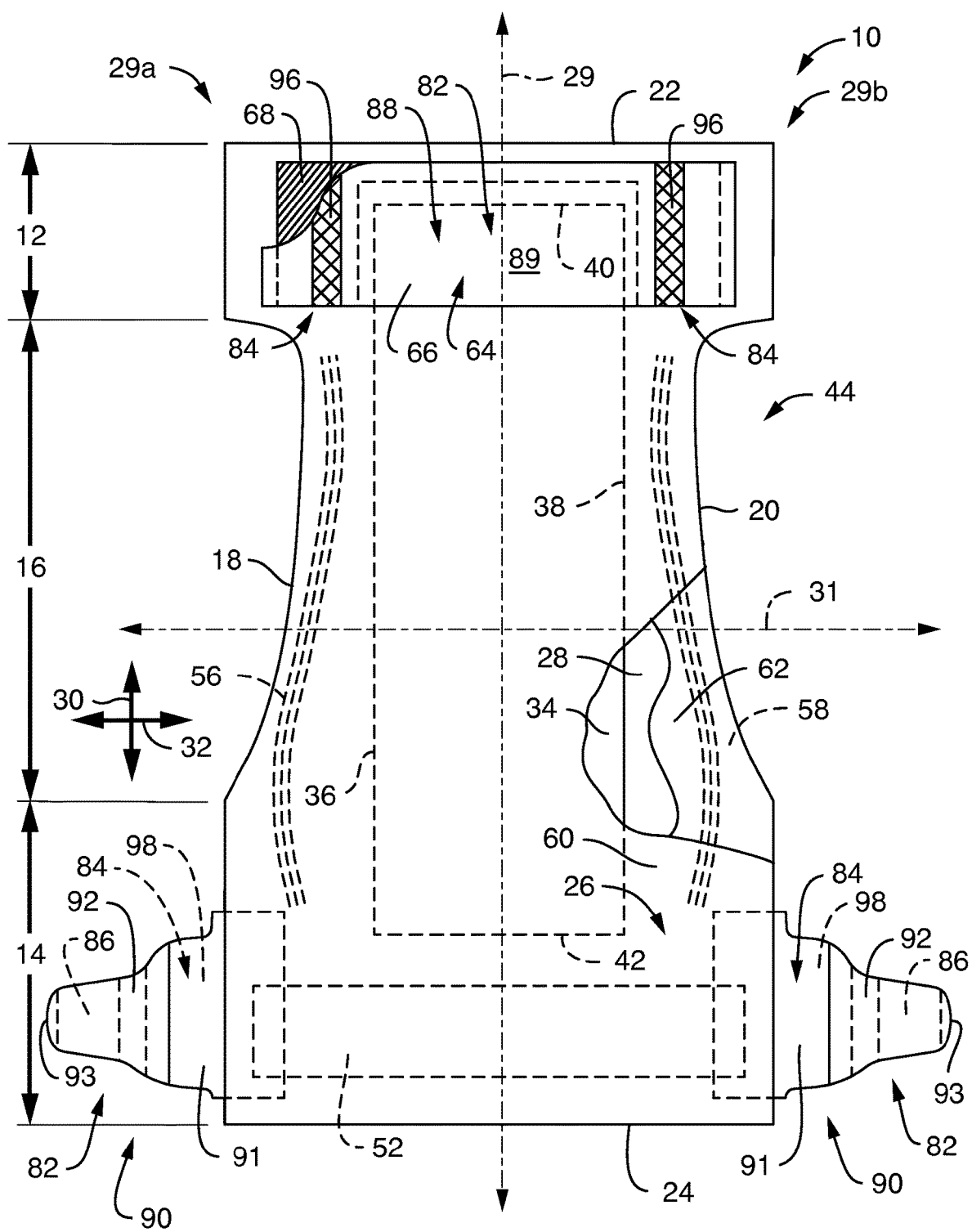
FIG. 1 is a top plan view of an exemplary embodiment of an absorbent article, such as a diaper, in a stretched, laid flat condition.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article having a pocket disposed on the outer surface in the front waist region of the absorbent article and a fastening system including a primary fastening system and a secondary fastening system. The pocket can aid a caregiver with providing an initial cleaning of the wearer after the article is soiled by the wearer and prior to changing the absorbent article. In preferred embodiments, the selective location of some components of the secondary fastening system can provide advantages for maintaining the tension and/or fit of the article on the wearer, even if the location of the primary fastening system moves affecting the initial tension and/or fit. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions:

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, training pant, youth pant, incontinent product, or other absorbent article about the wearer of one of these absorbent articles. A user and a wearer can be one and the same person.

Absorbent Article:

Referring to FIGS. 1-4, a non-limiting illustration of an absorbent article 10, for example, a diaper, is illustrated. Other embodiments of the absorbent article could include training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

The absorbent article 10 illustrated in FIG. 1 includes a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. The absorbent article 10 has a pair of longitudinal side edges, 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24.

The front waist region 12 can include the portion of the absorbent article 10 that, when worn, is positioned at least in part on the front of the wearer while the rear waist region 14 can include the portion of the absorbent article 10 that, when worn, is positioned at least in part on the back of the wearer. The crotch region 16 of the absorbent article 10 can include the portion of the absorbent article 10, that, when worn, is positioned between the legs of the wearer and can partially cover the lower torso of the wearer. The waist edges, 22 and 24, of the absorbent article 10 are configured to encircle the waist of the wearer and together define a central waist opening for the waist of the wearer. Portions of the longitudinal side edges, 18 and 20, in the crotch region 16 can generally define leg openings for the legs of the wearer when the absorbent article 10 is worn.

The absorbent article 10 can include an outer cover 26 and a bodyside liner 28, the bodyside liner 28 being depicted in the cut-away portion of FIG. 1. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated embodiment, can coincide with the length and width of the absorbent article 10. As illustrated in FIG. 1, the absorbent article 10 can have a longitudinal axis 29 extending in the longitudinal direction 30 and a lateral axis 31 extending in the lateral direction 32.

An absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10. The absorbent body 34 can have opposite first and second end edges, 40 and 42, respectively, which, in an embodiment, can form portions of the waist edges, 22 and 24, respectively, of the absorbent article 10. The first end edge 40 can be in the front waist region 12. The second end edge 42 can be in the rear waist region 14. In an embodiment, the absorbent body 34 can have a length and width that are the same as or less than the length and width of the absorbent article 10. The bodyside liner 28, the outer cover 26, and the absorbent body 34 can form part of an absorbent assembly 44. The absorbent assembly 44 can also include other components not shown herein, such as a fluid transfer layer and a fluid acquisition layer, as are known in the art.

The absorbent article 10 can be configured to contain and/or absorb liquid, solid, and semi-solid body exudates discharged from the wearer. For example, containment flaps (not shown), which are known in the art, can be configured to provide a barrier to the lateral flow of body exudates. To further enhance containment and/or absorption of body exudates, in some embodiments the absorbent article 10 can suitably include a waist elastic member, such as a rear waist elastic member 52. In some embodiments, the absorbent article 10 can include a front waist elastic member, although one is not depicted herein. The absorbent article 10 can further include leg elastic members, 56 and 58, as are known to those skilled in the art. The rear waist elastic member 52 can be attached to the outer cover 26 and/or the bodyside liner 28 along the rear waist edge 24 and can extend over part or all of the rear waist edge 24. In an embodiment shown in FIGS. 1 and 2, the rear waist elastic member 52 is attached to the bodyside liner 28. The leg elastic members, 56 and 58, can be attached to the outer cover 26 and/or the bodyside liner 28 along the opposite longitudinal side edges, 18 and 20, and positioned in the crotch region 16 of the absorbent article 10. The leg elastic members, 56 and 58, can be curved as shown in FIG. 1, or can be parallel to the longitudinal axis 29 as is known in the art.

Additional details regarding each of these elements of the absorbent article 10 described herein can be found below and with reference to the FIGS. 1 through 7.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In an embodiment, such as that shown in FIGS. 1-4, the outer cover 26 can be a two layer construction, including an outer layer 60 material and an inner layer 62 material (see FIG. 1) which can be bonded together such as by a laminate adhesive. Suitable laminate adhesives can be applied continuously or intermittently as beads, a spray, parallel swirls, or the like, but it is to be understood that the inner layer 62 can be bonded to the outer layer 60 by other bonding methods, including, but not limited to, ultrasonic bonds, thermal bonds, pressure bonds, or the like.

The outer layer 60 of the outer cover 26 can be any suitable material and may be one that provides a generally cloth-like texture or appearance to the wearer. An example of such material can be a 100% polypropylene bonded-carded web with a diamond bond pattern available from Sandler A. G., Germany, such as 30 gsm Sawabond 4185® or equivalent. Another example of material suitable for use as an outer layer 60 of an outer cover 26 can be a 20 gsm spunbond polypropylene non-woven web. The outer layer 60 may also be constructed of the same materials from which the bodyside liner 28 can be constructed as described herein.

The liquid impermeable inner layer 62 of the outer cover 26 (or the liquid impermeable outer cover 26 where the outer cover 26 is of a single-layer construction) can be either vapor permeable (i.e., "breathable") or vapor impermeable. The liquid impermeable inner layer 62 (or the liquid impermeable outer cover 26 where the outer cover 26 is of a single-layer construction) can be manufactured from a thin plastic film. The liquid impermeable inner layer 62 (or the liquid impermeable outer cover 26 where the outer cover 26 is of a single-layer construction) can inhibit liquid body exudates from leaking out of the absorbent article 10 and wetting articles, such as bed sheets and clothing, as well as the wearer and caregiver.

Where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Figure 2:
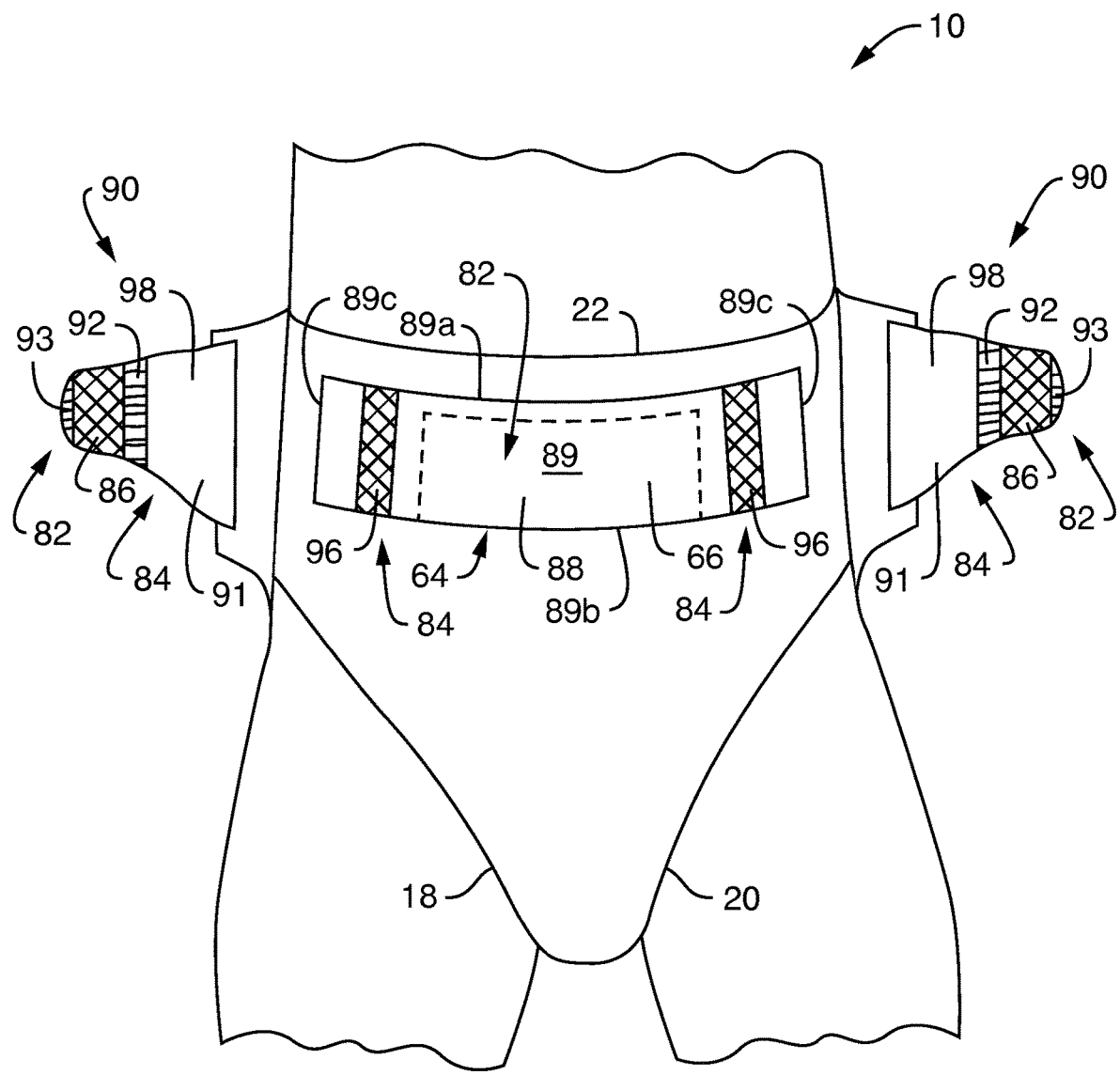
FIG. 2 is a perspective view of the absorbent article of FIG. 1 being donned on a wearer.
Figure 3:
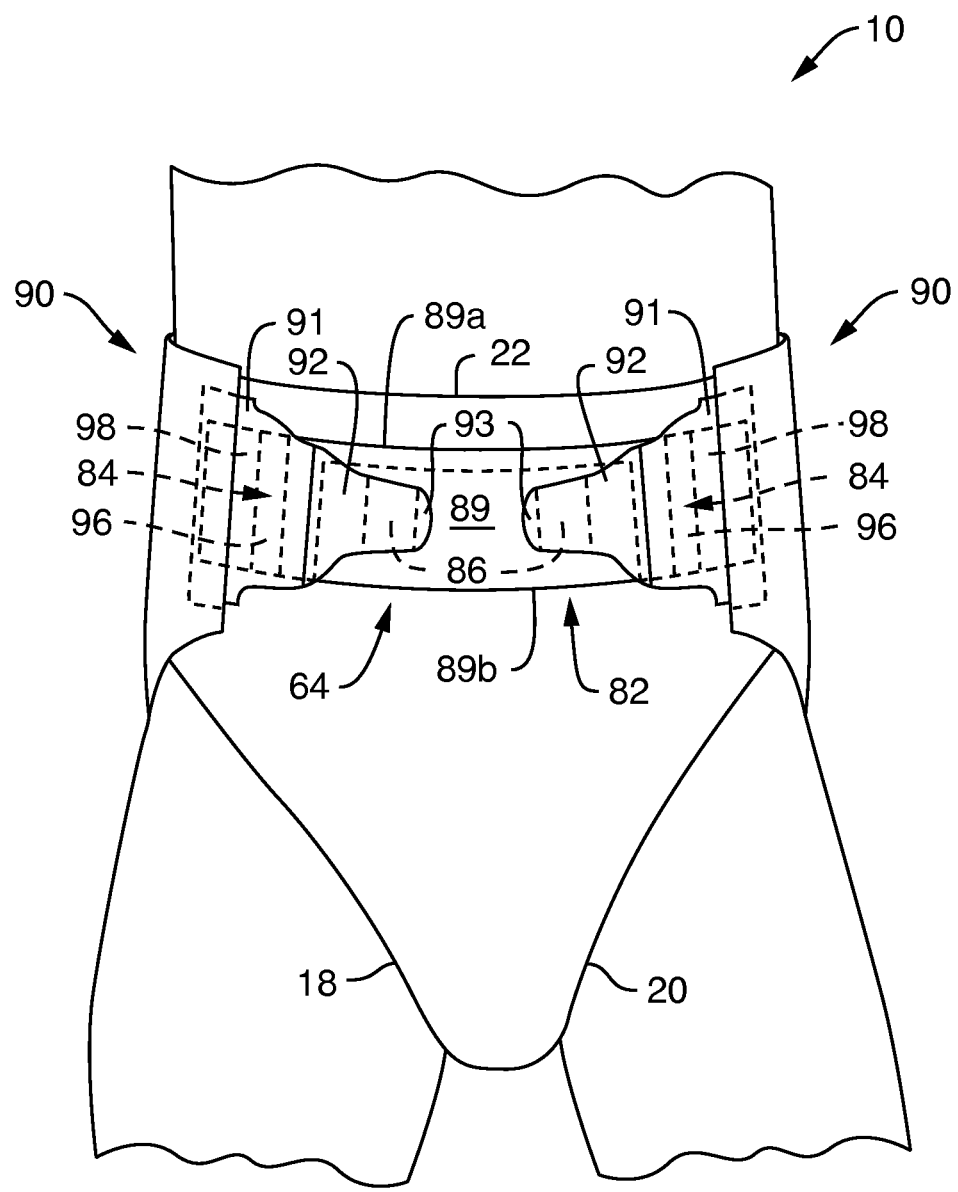
FIG. 3 is a perspective view of the absorbent article of FIG. 1 in a fastened condition on a wearer.
Figure 4:
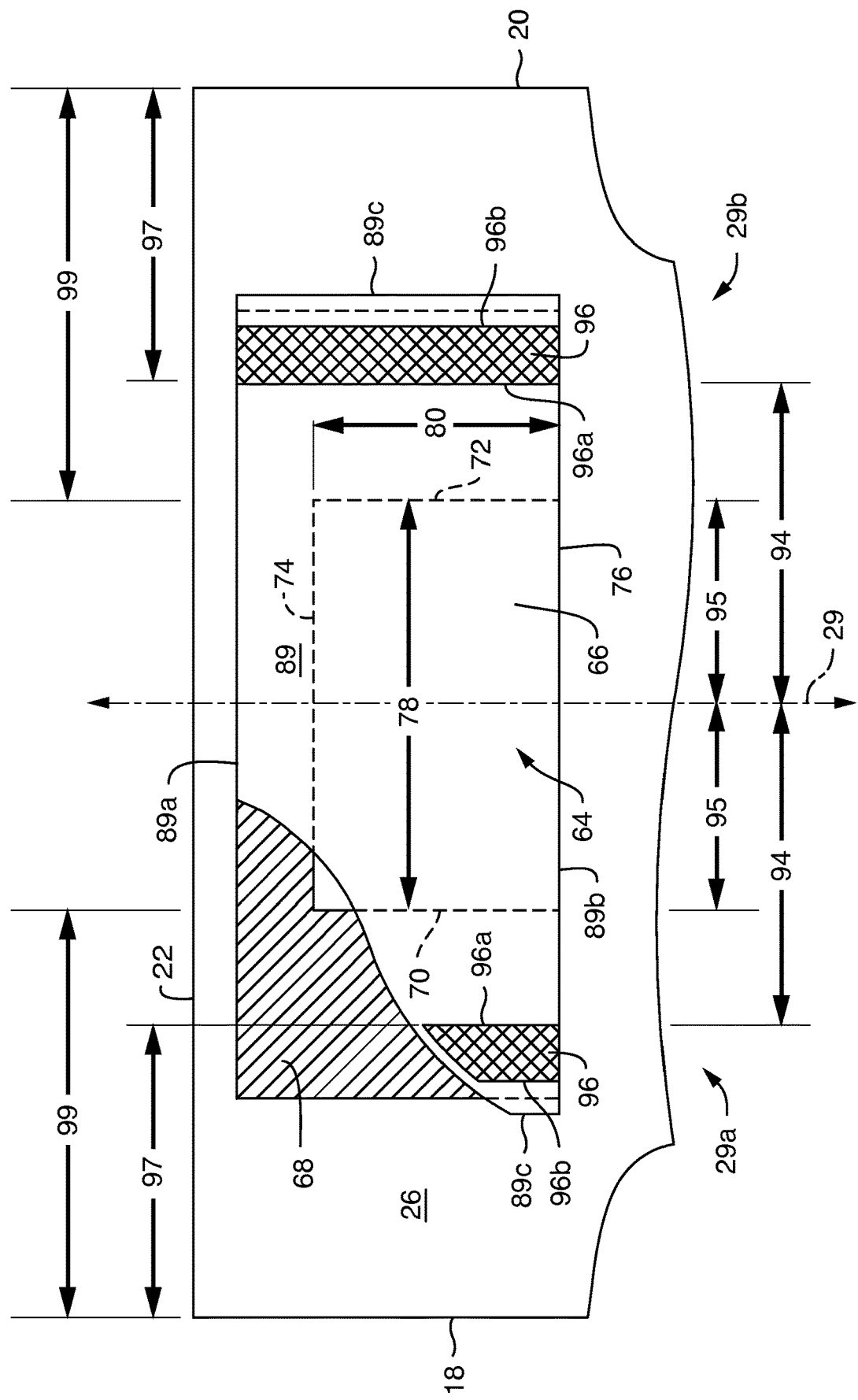
FIG. 4 is a detailed view of the front waist region of the absorbent article of FIG. 1.

As shown in FIGS. 1-4, a pocket 64 can be disposed in the front waist region 12 of the absorbent article 10. In some embodiments, the pocket 64 can be formed from a pocket material 66 coupled to the outer cover 26. The pocket material 66 can be coupled to the outer cover 26 by any suitable method known in the art, such as by adhesive 68, as shown in FIGS. 1 and 4.

As illustrated in FIG. 4, the pocket 64 can include a first side edge 70 and a second side edge 72. The second side edge 72 can be opposite from the first side edge 70. The pocket 64 can also include an upper lateral edge 74 and a lower lateral edge 76. The pocket 64 can be closed with respect to the absorbent assembly 44 at the first side edge 70, the second side edge 72, and the upper lateral edge 74. As shown in the embodiment depicted in FIGS. 1-4, the pocket 64 is closed with respect to the absorbent assembly 44 in this manner due to the selective location of the adhesive 68. The pocket 64 can be open with respect to the absorbent assembly 44 at the lower lateral edge 76. The open nature of the pocket 64 at the lower lateral edge 76 allows a caregiver's hand to enter the pocket 64 to assist with an initial wiping of the skin of the wearer after the article 10 becomes soiled with exudates prior to disposing of the soiled absorbent article 10 and cleansing the wearer's skin. In some embodiments, the pocket 64 can be open with respect to absorbent assembly 44 at the upper lateral edge 74 as well as at the lower lateral edge 76.

The pocket 64 can be disposed in the front waist region 12 of the absorbent article 10 with particular positioning with respect to the absorbent body 34 to provide an enhanced ability for the caregiver to maintain their hand in the pocket 64 and grip during wiping of a wearer of the absorbent article 10. In one respect, the pocket 64 can be disposed in the front waist region 12 such that at least a portion of the upper lateral edge 74 of the pocket 64 is closer to the front waist edge 22 of the absorbent article 10 than is the first end edge 40 of the absorbent body 34. Configuring the pocket 64 such that at least a portion of the upper lateral edge 74 is closer to the front waist edge 22 than is the first end edge 40 of the absorbent body 34 provides a gap between the upper lateral edge 74 of the pocket 64 and the first end edge 40 of the absorbent body 34. This gap can provide room for one or more of a caregiver's fingers to rest against the first end edge 40 of the absorbent body 34 when the caregiver's fingers are inserted into the pocket 64 and provides enhanced gripping and control of the pocket 64.

The pocket 64 can also be selectively designed to have width 78 and length 80 configurations that provide enhanced handling and control of the pocket 64 when wiping the wearer of the absorbent article 10. As used herein, the length 80 of the pocket 64 is measured between the upper lateral edge 74 of the pocket 64 to the lower lateral edge 76 of the pocket 64 in a direction parallel to the longitudinal axis 29 of the absorbent article 10. As used herein, the width 78 of the pocket 64 is measured between the first side edge 70 of the pocket 64 and the second side edge 72 of the pocket 64 in a direction parallel to the lateral axis 31 of the absorbent article 10. In preferred embodiments, the length 80 of the pocket 64 is preferably configured to be between about 1.25 inches and about 3.75 inches, and more preferably between about 2.00 inches and about 3.00 inches. In a preferred embodiment, the length 80 of the pocket 64 can be about 2.50 inches. Furthermore, the width 78 of the pocket 64 is preferably configured to be between about 3.00 inches and about 6.00 inches, and more preferably between about 3.50 inches and about 4.50 inches. In a preferred embodiment, the width 78 of the pocket 64 can be about 4.00 inches.

The pocket 64 can be designed to be of various shapes. For example, in the embodiment shown in FIGS. 1-4, the pocket 64 can be generally rectangular in shape with the first side edge 70 being parallel to the second side edge 72 of the pocket 64 and the upper lateral edge 74 being parallel to the lower lateral edge 76. The upper and lower lateral edges 74, 76, respectively, can be parallel to the lateral axis 31 of the absorbent article 10. However, in some embodiments, the first and second side edges 70, 72 and/or the upper and lower lateral edges 74, 76 can be curved.

Although the pocket 64 can be formed with pocket material 66 that is coupled to the outer cover 26 of the absorbent article 10 such as with adhesive 68 (as shown in FIGS. 1, 2, and 4-7), the pocket 64 can be formed in other ways and is not limited to such a configuration the pocket 64 can be formed between two layers 60, 62 of the outer cover 26, where the outer layer 60 is not adhered to the inner layer 62. The lower lateral edge 76 of the pocket 64 can be formed by a slit in the outer layer 60 of the outer cover 26.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. For example, FIGS. 1 and 2 illustrate an absorbent body 34 that is rectangular in shape, with a first end edge 40 and second end edge 42 that are parallel to one another and the lateral axis 31. However, one or more of the first and second end edges 40, 42 and the longitudinal edges 36, 38 of the absorbent body 34 can be curved. The size and the absorbent capacity of the absorbent body 34 should be compatible with the size of the intended wearer (infants to adults) and the liquid loading imparted by the intended use of the absorbent article 10. The absorbent body 34 can have a length and width that can be less than or equal to the length and width of the absorbent article 10. The absorbent body 34 can have longitudinal side edges, 36 and 38, and front and back end edges, 40 and 42.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material.

The absorbent body 34 can be superposed over the inner layer 62 of the outer cover 26 and can be bonded to the inner layer 62 of the outer cover 26, such as by being bonded thereto with adhesive. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In an embodiment, a layer, such as but not limited to, a fluid transfer layer (not shown), can be positioned between the absorbent body 34 and the outer cover 26.

Bodyside Liner:

The bodyside liner 28 of the absorbent article 10 can overlay the absorbent body 34 and the outer cover 26 and can isolate the wearer's skin from liquid waste retained by the absorbent body 34. In various embodiments, a fluid transfer layer (not shown) can be positioned between the bodyside liner 28 and the absorbent body 34. In various embodiments, an acquisition layer (not shown) can be positioned between the bodyside liner 28 and the absorbent body 34 or a fluid transfer layer, if present. In various embodiments, the bodyside liner 28 can be bonded to the acquisition layer, or to the fluid transfer layer if no acquisition layer is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer, if present, and/or an acquisition layer, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. The bodyside liner 28 may be narrower than the outer cover 26, but it is to be understood that the bodyside liner 28 and the outer cover 26 may be of the same dimensions. It is also contemplated that the bodyside liner 28 may not extend beyond the absorbent body 34 and/or may not be secured to the outer cover 26. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Patent Application Publication No. 2014/0121623 invented by Kirby, Scott S. C. et al. In a preferred embodiment, the bodyside liner 28 includes a bodyfacing surface that provides an uneven surface at least in the front waist region 12, such as a bodyfacing surface that includes projections as disclosed in U.S. Patent Application Publication No. 2014/0121623 noted above. Such a bodyfacing liner provides additional benefits in softness and assists in cleaning the wearer's skin when the caregiver uses the pocket 64 of the absorbent article 10 to wipe the wearer.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10. In other aspects, the bodyside liner 28 can be stretchable, and more suitably elastic, in both the lateral and the longitudinal directions 32, 30, respectively.

Leg Elastics:

Leg elastic members 56, 58 (labeled in FIG. 1) can be secured to the outer cover 26, such as by being bonded thereto by laminate adhesive, generally laterally inward of the longitudinal side edges, 18 and 20, of the absorbent article 10. The leg elastic members 56, 58 can form elasticized leg cuffs that further help to contain body exudates. In an embodiment, the leg elastic members 56, 58 may be disposed between the inner layer 62 and outer layer 60 of the outer cover 26 or between other layers of the absorbent article 10. The leg elastic members 56, 58 can be a single elastic member, or each leg elastic member 56, 58 can include more than one elastic member, such as illustrated herein. A wide variety of elastic materials may be used for the leg elastic members 56, 58. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Of course, the leg elastic members 56, 58 can be omitted from the absorbent article 10 without departing from the scope of this disclosure.

Fastening System:

In an embodiment, the absorbent article 10 can include a fastening system. The fastening system can include a primary fastening system 82 and a secondary fastening system 84. The primary fastening system 82 can include at least one primary first fastening component 86 and at least one primary second fastening component 88. As shown in FIGS. 1-3, a preferred embodiment of an absorbent article 10 can include two primary first fastening components 86, with one primary first fastening component 86 being on each back ear 90 in the rear waist region 14. The primary second fastening component 88 can be disposed in the front waist region 12. In the embodiment depicted in FIGS. 1-4, the primary fastening system 82 includes only one primary second fastening component 88, however, it is to be noted that a primary fastening system 82 could include more than one primary second fastening component 88.

In some embodiments, the outer facing surface of the outer cover 26 of the diaper 10 is suitably constructed to define the primary second fastening component 88, which is a loop fastener. That is, the outer cover 26 itself can be formed of a material that defines the primary second fastening component 88 (e.g., vertical filament laminate (VFL) or other suitable material).

In another suitable embodiment, and as illustrated in FIGS. 1-4, the primary second fastening component 88 can be formed as a separate component and attached to the outer surface of the diaper's outer cover 26. More specifically, a strip, indicated generally at 89, comprising loop fastening material is attached to the front waist region 12 of the article 10. The strip 89 of material forming the primary second fastening component 88 comprises an upper edge 89a, a lower edge 89b, and a pair of side edges 89c connecting the upper and lower edges 89a, 89b. The upper edge 89a can be spaced from the front waist edge 22 and the side edges 89c can be spaced from the respective side edges 18, 20 of the article 10. Advantageously, the strip 89 of material forming the primary second fastening component 88 can also form the pocket material 66, which forms the pocket 64 described above. Designing the strip 89 to be the same material as the pocket material 66 provides efficiencies and cost savings in that one material assists with the fastening of the absorbent article 10 as well as provides utility for assisting the caregiver with wiping the wearer after the article 10 becomes soiled.

In one suitable embodiment, in addition to including a primary first fastening component 86, each of the back ears 90 can include an elastomeric portion 91 and a non-elastomeric portion 92. As can be seen in FIGS. 1-3, the elastomeric portion 91 of each ear 90 can overlap the side edge 18, 20 and be bonded to the bodyside liner 28 (e.g., adhesive bonding, pressure bonding, thermal bonding, or combination thereof). In other suitable embodiments, the elastomeric portion 91 can be eliminated and the entire back ear 90 can include one or more non-elastomeric portion(s) 92. FIGS. 1-3 depict that the elastomeric portions 91 and the non-elastomeric portions 92 of the back ears 90 can be non-rectangular shaped, however, it can be appreciated that the elastomeric portion 91 and the non-elastomeric portion 92 of one or more of the back ears 90 can be rectangular shaped or any other suitable shape. Each of the non-elastomeric portions 92 of the back ears 90 is attached to a respective one of the elastomeric portions 91, and the primary first fastening components 86 are in turn disposed on the non-elastomeric portions 92. As illustrated in FIGS. 1-3, the non-elastomeric portions 92 of the back ears 90 extend in part transversely outward of the respective elastomeric portion 91 and the primary first fastening component 86 are configured for engaging the primary second fastening component 88 in the front waist region 12 of the article 10, such as shown in FIG. 3 and as will be discussed further below. A small grip region 93 extends transversely outward from the respective primary first fastening component 86, such that it can provide sufficient unattached material for readily gripping and pulling on the non-elastomeric portion 92 to unfasten the primary first fastening components 86 from the primary second fastening component 88.

The primary first fastening components 86 are adapted for refastenable engagement with the primary second fastening component 88, such that the primary first fastening components 86 are engaged with the primary second fastening component 88 when the article 10 is in a fastened condition (as shown in FIG. 3), and are not engaged with the primary second fastening component 88 when the article 10 is in an unfastened condition (as shown in FIG. 2). The primary first fastening components 86 and the primary second fastening component 88 can comprise any refastenable fasteners suitable for absorbent articles, such as adhesive fasteners, cohesive fasteners, mechanical fasteners, or the like. In one suitable embodiment, the primary fastening components 86, 88 comprise mechanical fastening components, such as hook and loop fasteners. For example, suitable hook and loop components can be provided by interlocking geometric shaped materials. As used herein, "hook" broadly refers to any suitable mechanical fastener adapted to engage loop components including, e.g., hooks, bulbs, mushrooms, arrowheads, balls on stems, stems, structures having stems that engage foam such as open cell foam or the like, etc. Other suitable mechanical fastening components include male and/or female mating components, buckles, snaps, or the like. In the illustrated embodiment, the primary first fastening components 86 comprise hook fasteners and the primary second fastening component 88 comprises a complementary loop fastener disposed on the outer surface of the outer cover 26. Alternatively, the primary first fastening components 86 may comprise loop fasteners and the primary second fastening component 88 may comprise complementary hook fasteners.

The secondary fastening system 84 can include at least one secondary first fastening component 96 and at least one secondary second fastening component 98. As illustrated in the embodiments in FIGS. 1-7, the secondary fastening system 84 can include two secondary first fastening components 96 and two secondary second fastening components 98 in some embodiments. The secondary first fastening components 96 can be disposed in the front waist region 12 of the article 10. As depicted in FIGS. 1 and 4-7, one secondary first fastening component 96 can be disposed in the first longitudinal half 29a of the absorbent article 10, and the other secondary first fastening component 96 can be disposed in the second longitudinal half 29b of the absorbent article 10. The first longitudinal half 29a of the absorbent article 10 is separated from the second longitudinal half 29b of the absorbent article 10 by the longitudinal axis 29. The secondary first fastening components 96 are adapted for refastenable engagement to at least one corresponding secondary second fastening component 98 (e.g., the elastomeric portion 91 of the back ears 90) such that the secondary first fastening components 96 are engaged with the secondary second fastening component 98 when the article is in a fastened condition (as shown in FIG. 3), and are not engaged with the secondary second fastening component 98 when the article 10 is in an unfastened condition (as shown in FIG. 2).

Figure 5:
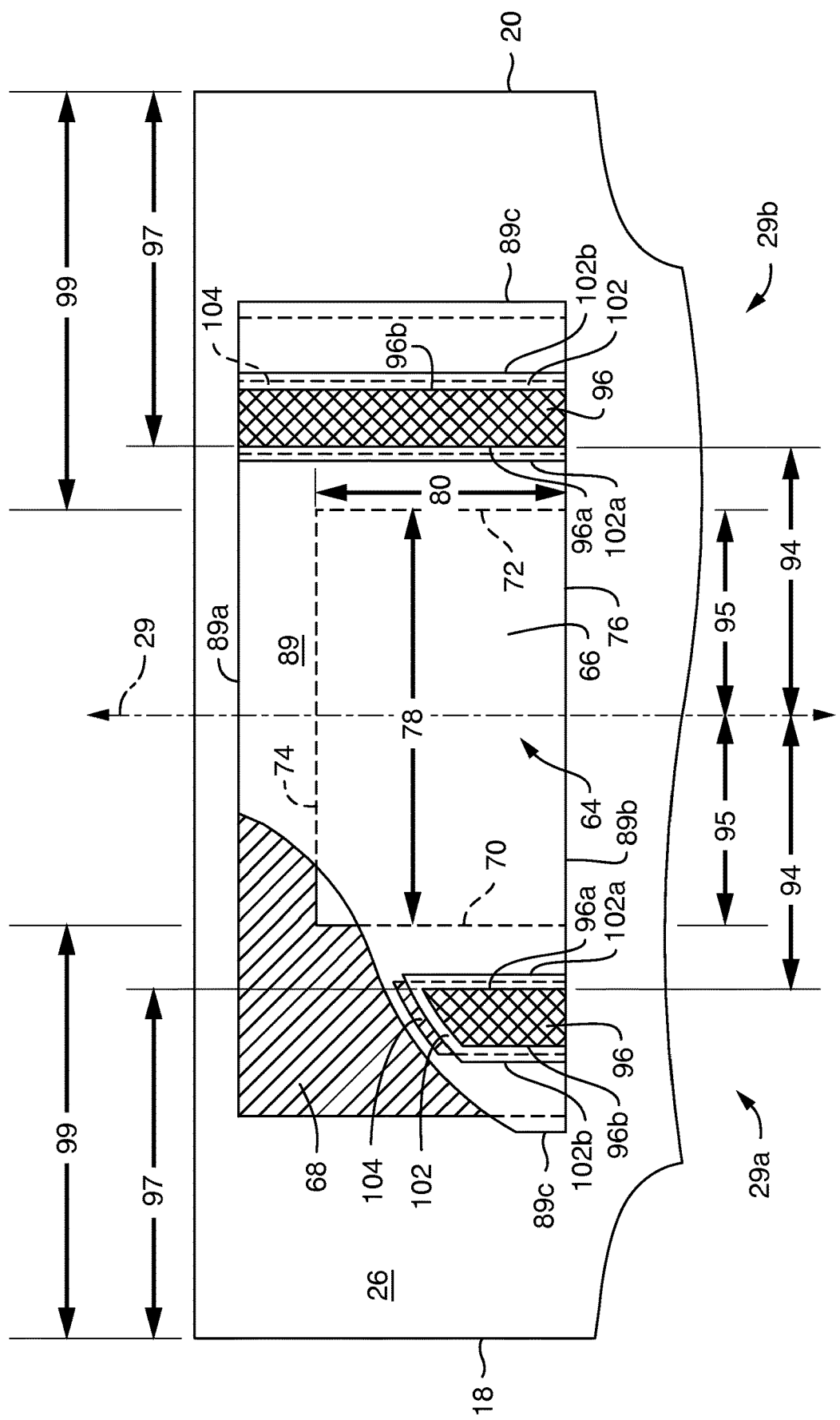
FIG. 5 is a detailed view of a front waist region of an alternative embodiment of an absorbent article.
Figure 6:
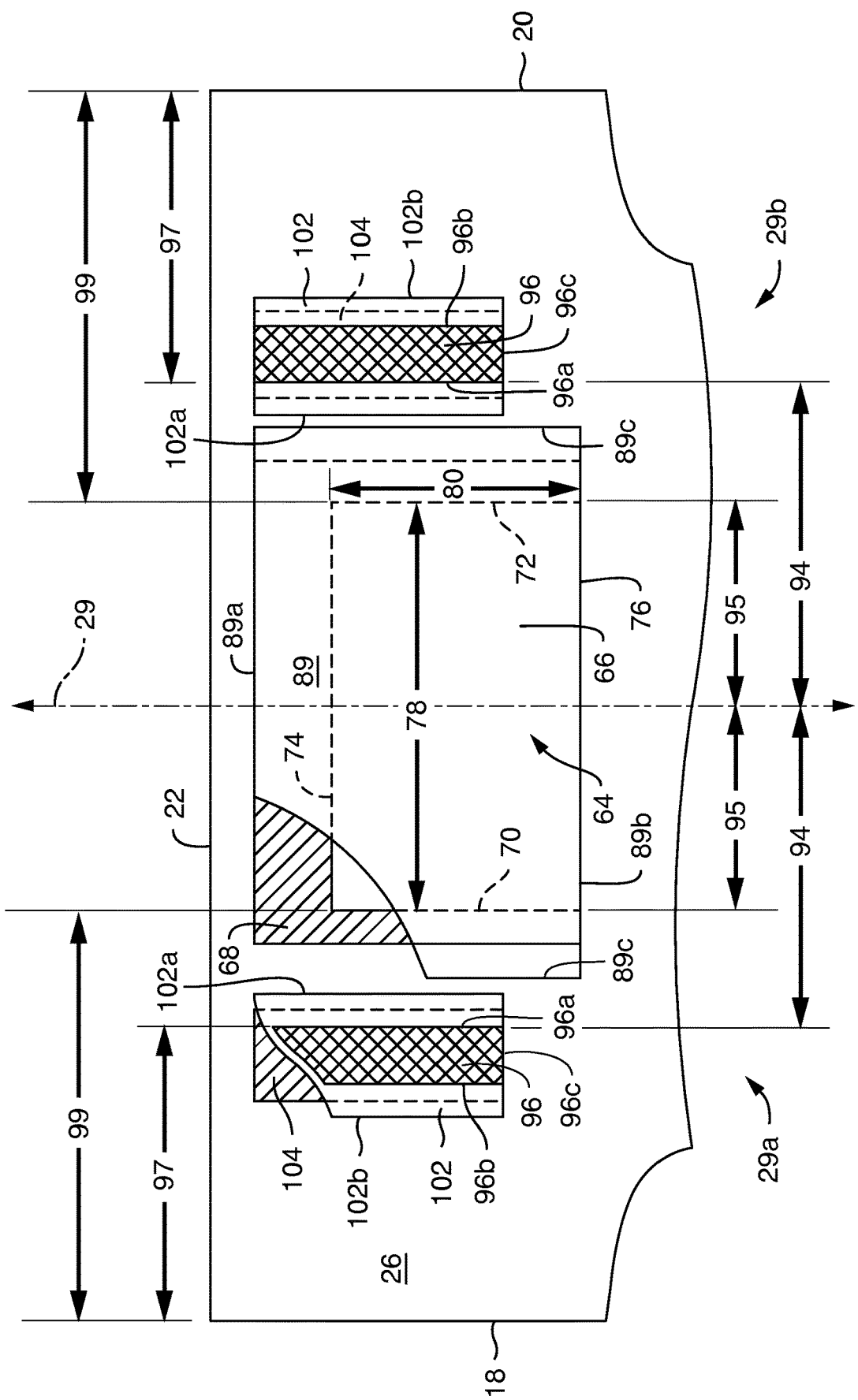
FIG. 6 is a detailed view of a front waist region of another alternative embodiment of an absorbent article.
Figure 7:
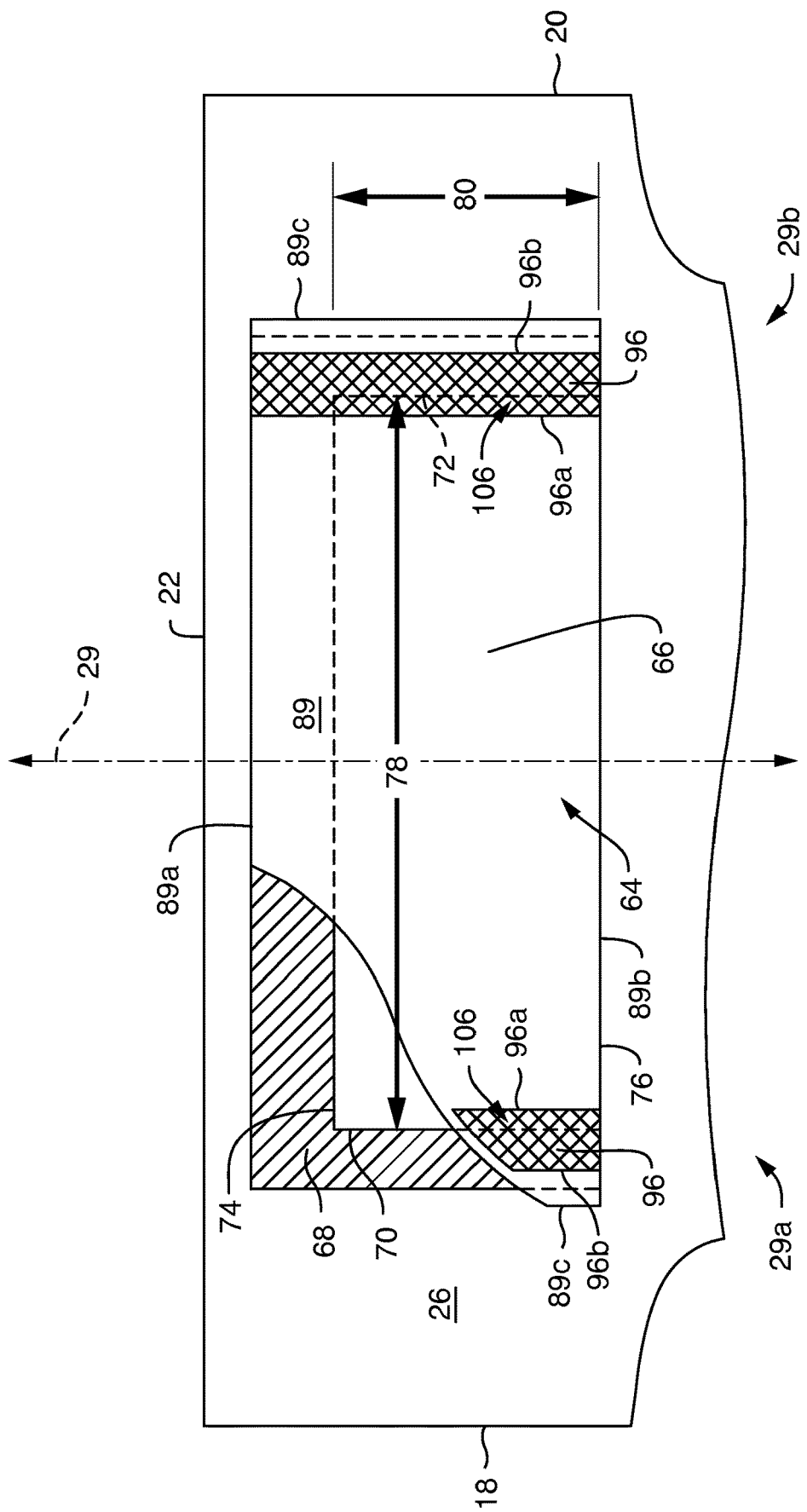
FIG. 7 is a detailed view of a front waist region of an yet another alternative embodiment of an absorbent article.

The secondary first fastening components 96 can include an inner longitudinal edge 96a and an outer longitudinal edge 96b, as illustrated in FIGS. 4-7. The secondary first fastening components 96 can be of various sizes and shapes and can each comprise an area, the area being defined as the area of space of the secondary first fastening component 96 provides in a plane horizontal to the outer cover 26 when the absorbent article 10 is in a stretched, laid flat condition, such as shown in FIGS. 1 and 4-7. In suitable embodiments, the secondary first fastening components 96 can be substantially rectangular in shape. In some embodiments, the strip 89 can comprise the pair of spaced-apart secondary first fastening components 96, such as illustrated in FIGS. 4 and 7.

In the illustrated embodiments herein, the secondary first fastening components 96 comprise hook fasteners and are configured to engage the secondary second fastening components 98 in the fastened condition of the article 10, as depicted in FIG. 3. Again, as used herein "hook" fasteners refers broadly to any suitable mechanical fastener adapted to engage loop components including, e.g., hooks, bulbs, mushrooms, arrowheads, balls on stems, stems, structures having stems that engage foam such as open cell foam or the like, etc. In one embodiment, the secondary first fastening components 96 may be constructed of polyethylene or other suitable polymer blends. In one suitable embodiment, the elastomeric portions 91 of the back ears 90 are constructed so at least the inner surfaces of the elastomeric portions define the secondary second fastening components 98 in the form of loop fastening components (i.e., the elastomeric portions and the respective secondary second fastening components are formed integrally). The elastomeric portions 91 in one suitable embodiment can be constructed of NBL material so that the elastomeric portion itself defines a loop fastening component. In another suitable embodiment, the elastomeric portions 91 can be constructed of VFL material so that the elastomeric portion itself defines a loop fastening component. It is understood, however, that the secondary second fastening components 98 may be formed separate from the elastomeric portions 91 and attached thereto, such as by adhesive, thermal bonds, ultrasonic bonds, pressure bonds, or other suitable techniques without departing from the scope of this disclosure.

In other suitable embodiments, the secondary first fastening components 96 may comprise loop fasteners and the secondary second fastening components 98 may comprise hook fasteners. Further, in some embodiments the secondary first fastening components 96 may be a single, integral fastener. For example, in one suitable embodiment the secondary first fastening components 96 may be a single, loop fastener, and the secondary second fastening components 98 may be hook fasteners.

In one suitable embodiment, such as shown in FIGS. 1-4 and 7, the strip 89 can comprise both the secondary first fastening components 96 and the primary second fastening component 88. In one such embodiment where the primary second fastening component 88 comprises a loop material and the secondary first fastening components 96 comprise a hook material, the strip 89 may be a suitable loop material (forming the primary second fastening component), and then the hook material may be extruded onto the loop material at two or more locations forming the secondary first fastening components 96. As discussed above, the strip 89 can be the same material that forms the pocket material 66 forming the pocket 64. In such embodiments, the strip 89 provides the efficiencies of forming portions of both the primary fastening system 82 and the secondary fastening system 84, as well as forming the pocket 64 that aids in cleaning the wearer after the article 10 becomes soiled.

In other suitable embodiments, such as those shown in FIGS. 5 and 6, the secondary first fastening components 96 can be coupled to corresponding carrier materials 102. The corresponding carrier materials 102 can be coupled to the strip 89 forming the primary second fastening component 88 (such as shown in FIG. 5) or the carrier materials 102 can be coupled directly to the outer cover 26 (such as shown in FIG. 6). In the embodiment depicted in FIG. 6, the carrier materials 102 can include an innermost edge 102a and an outermost edge 102b, with the carrier materials 102 being coupled to the outer cover 26 such that the innermost edge 102a of the carrier material 102 including the secondary first fastening component 96 in the first longitudinal half 29a is disposed laterally outside of the side edge 89c of the strip 89 in the first longitudinal half 29a and the innermost edge 102a of the carrier material 102 including the secondary first fastening component 96 in the second longitudinal half 29b is disposed laterally outside of the side edge 89c of the strip 89 in the second longitudinal half 29b. Of course, it is to be appreciated that in other embodiments, one or more of the carrier materials can be configured such that a portion of the carrier material 102 can be coupled to the strip 89 and another portion of the carrier material 102 can be coupled directly to the outer cover 26 such that the innermost edge 102a of the carrier material 102 laterally overlaps with the respective side edges 89c of the strip 89. The carrier materials 102 can be coupled to the strip 89 and/or the outer cover 26 with adhesive 104 as illustrated in FIGS. 5 and 6, although the carrier materials 102 can be coupled to the strip 89 and/or the outer cover 26 by other means as is known in the art (e.g., pressure bonding, ultrasonic bonding, stitching, etc.).

Providing the secondary first fastening components 96 on carrier materials 102 can provide advantages for the absorbent article 10. For example, carrier materials 102 can provide additional strength and stiffness to the overall absorbent article 10 in the area of the carrier material 102. In some embodiments, this additional strength and stiffness to the overall absorbent article 10 can provide the benefit of helping the absorbent article 10 maintain its position on the wearer during a wear configuration, e.g., reduce the sagging or drooping of the absorbent article 10. Additionally, providing the secondary first fastening component 96 on a carrier material 102 that does not form the strip 89 comprising the primary second fastening component 88 can provide cost savings in processing and converting the secondary first fastening component 96 on the carrier material 102 in roll form as compared to the cost of processing and converting the secondary first fastening component 96 when the secondary first fastening component 96 is on the strip 89. This advantage can be realized because providing the secondary first fastening component 96 on the carrier material 102 provides for the possibility of spacing the material forming the secondary first fastening component 96 more densely on to the material that will form the carrier material 102 as compared to providing the secondary first fastening components 96 directly on the material forming the primary second fastening component 88, where the spacing between secondary first fastening components 96 may be dictated by the designed spacing between the secondary first fastening components 96 in the front waist region 12 of the absorbent article 10. Furthermore, providing the secondary first fastening components 96 on a carrier material 102 can provide the ability to dispose the secondary first fastening components 96 further towards the longitudinal side edges 18, 20 of the absorbent article 10 in a more cost-effective manner in comparison to increasing the width of the strip 89.

Providing the secondary first fastening components 96 on carrier materials 102 can also provide another advantage related to the longitudinal length of the secondary first fastening components 96. Specifically, as illustrated in FIG. 6, the secondary first fastening components 96 can have a bottom edge 96c that is closer to the front waist edge 22 than the lower lateral edge 76 of the pocket 64 is to the front waist edge 22. This provides the advantage of keeping the secondary first fastening components 96 further away from the longitudinal side edges 18, 20 of the article 10, which can help reduce irritation to the wearer. It is to be noted that having a secondary first fastening component 96 with a bottom edge 96c closer to the front waist edge 22 than is the lower lateral edge 76 of the pocket 64 can also be accomplished without the use of carrier materials 102 (such as embodiments depicted in FIGS. 1-4 and 7) or where the carrier material 102 is directly coupled to the material 66 forming the pocket 64 (as depicted in FIG. 5) by modifying the length and/or positioning of the secondary first fastening components 96 with respect to the pocket 64. However, having the carrier materials 102 including the secondary first fastening components 96 not directly coupled to the material 66 forming the pocket 64 (which can also form the primary second fastening component 88), allows the length of the secondary first fastening components 96 to be controlled by controlling the length and/or positioning of the carrier material 102 independent from the longitudinal length of the material 66 forming the pocket 64. Thus, such a configuration including carrier materials 102 may provide for additional benefits in controlling the longitudinal length and/or longitudinal positioning of the secondary first fastening component 96 during manufacturing of the absorbent article 10, but is not required to establish the described relationship between the bottom edge 96c of the secondary first fastening component 96 and the lower lateral edge 76 of the pocket 64 and the advantages to the wearer stemming therefrom.

Regardless of the execution of how the secondary first fastening components 96 are configured on the absorbent article 10, when the absorbent article 10 is moved to the fastened configuration as illustrated in FIG. 3 with the primary fastening components 86, 88 engaging one another, the secondary fastening components 96, 98 may also engage one another in order to provide increased stability and leakage protection. For example, because the article fastening system comprises four engagement points, the absorbent article 10 will be less prone to pop-opens when worn. Further, because the secondary fastening components 96, 98 engage each other closer to a side of a wearer than an engagement point of the primary fastening components 86, 88, the secondary fastening system 84 secures the absorbent article 10 nearer the wearer's sides and legs thus reducing leakage near the leg openings of the article 10. Still further, and again because the secondary fastening components 96, 98 engage each other near a side of the wearer, the secondary fastening system 84 may provide increased stability, thus reducing the occurrence of, e.g., sagging of the diaper due to movement of the wearer.

The secondary fastening system 84 provides advantages to reduce tension loss and reduction in fit properties of the absorbent article due to some configurations of the interaction between the primary fastening system 82 and the pocket 64. As shown in FIG. 3, in some embodiments the pocket 64 of the absorbent article 10 can be configured such the primary first fastening components 86 can engage the pocket 64, especially where the pocket material 66 is the same as the strip 89 comprising the primary second fastening component 88. In such a circumstance, the location of the primary fastening system 82 may move and may affect the initial tension and fit applied to the primary fastening components 86, 88 because the primary second fastening component 88 can move with respect to the absorbent assembly 44. Such a circumstance can also be applicable where the strip 89 of primary second fastening component 88, does not form all of the pocket material 66 for the pocket 64, but is directly bonded to the pocket material 66 and the primary fastening components 86, 88 engage one another in the location of the pocket 64. By having the secondary fastening system 84 selectively located on the absorbent article 10, the secondary first fastening components 96 and the secondary second fastening components 98 can help prevent a loss in tension of fastening system of the absorbent article 10 and a loss in the initially applied fit to the absorbent article 10.

For example, as best shown in FIGS. 4-6, the secondary first fastening components 96 can be selectively located with respect to the pocket 64 such that at least a portion of the inner longitudinal edge 96a is located laterally outside of the respective side edges 70, 72 of the pocket 64. As illustrated in FIG. 4, the inner longitudinal edge 96a of the secondary first fastening component 96 in the first longitudinal half 29a of the absorbent article 10 has the entire length of the inner longitudinal edge 96a laterally outside of the first side edge 70 of the pocket 64. Similarly, the inner longitudinal edge 96a of the secondary first fastening component 96 in the second longitudinal half 29b of the absorbent article 10 has the entire length of the inner longitudinal edge 96a laterally outside of the second side edge 72 of the pocket 64. Stated in different terms, at least a portion of the inner longitudinal edge 96a of each of the secondary first fastening components 96 is laterally further from the longitudinal axis 29 than is the respective side edge 70, 72 of the pocket 64. Thus, a distance 94 between the longitudinal axis 29 and the inner longitudinal edge 96a of the secondary first fastening component 96 is greater than a distance 95 between the longitudinal axis 29 and the respective side edge 70, 72 of the pocket 64. It can be appreciated that although the distance 95 between the longitudinal axis 29 and the respective side edge 70, 72 of the pocket 64 is the same for the secondary first fastening component 96 in the first longitudinal half 29a as for the secondary first fastening component 96 in the second longitudinal half 29b, such symmetry need not be the case to still satisfy this condition. By selectively locating the secondary first fastening components 96 with respect to the respective side edges 70, 72 of the pocket 64 as described above, the secondary first fastening components 96 do not move with respect to the absorbent assembly 44, and as a result, provide stability for the absorbent article 10 in the fastened condition, even if the location of the primary fastening system 82 moves affecting the initial tension and/or fit.

Additionally, the inner longitudinal edges 96a are laterally closer to the respective longitudinal edges 18, 20 of the absorbent article 10 than are the side edges 70, 72 of the pocket 64. For example, as illustrated in FIGS. 4-6, the distance 97 between the inner longitudinal edge 96a of the secondary first fastening component 96 in the first longitudinal half 29a of the absorbent article 10 and the longitudinal side edge 18 of the absorbent article 10 is less than the distance 99 between the first side edge 70 of the pocket 64 and the longitudinal side edge 18 of the absorbent article 10. Similarly, the distance 97 between the inner longitudinal edge 96a of the secondary first fastening component 96 in the second longitudinal half 29b of the absorbent article 10 and the longitudinal side edge 20 of the absorbent article 10 is less than the distance 99 between the second side edge 72 of the pocket 64 and the longitudinal side edge 20 of the absorbent article 10. Again, it can be appreciated that although the distance 97 between the inner longitudinal edge 96a and the respective longitudinal side edge 18, 20 of the absorbent article 10 is the same for the secondary first fastening component 96 in the first longitudinal half 29a as for the secondary first fastening component 96 in the second longitudinal half 29b, such symmetry need not be the case to satisfy this condition. By selectively locating the secondary first fastening components 96 such that the inner longitudinal edges 96a are laterally closer to the respective longitudinal edges 18, 20 than are the side edges 70, 72 of the pocket 64, the secondary first fastening components 96 do not move with respect to the absorbent assembly 44, and as a result, provide stability for the absorbent article 10 in the fastened condition, even if the location of the primary fastening system 82 moves affecting the initial tension and/or fit.

In some embodiments, as best illustrated in FIGS. 4-7, the secondary first fastening components 96 can be located such that at least a majority of the area of the secondary first fastening components 96 are outside of the pocket 64. In some embodiments, such as in FIGS. 4-6, the secondary first fastening components 96 can be located such that all of the area of the secondary first fastening components 96 are outside of the pocket 64. In some embodiments, such as in FIGS. 4-7, at least a majority of the secondary first fastening components 96 can be located laterally outside of the pocket 64. In some embodiments, such as in FIGS. 4-6, the secondary first fastening components 96 can be located such that all of the area of the secondary first fastening components 96 are laterally outside of the pocket 64.

FIG. 7 depicts an embodiment where a portion 106 of the area of each of the secondary first fastening components 96 is located inside of the pocket 64 (i.e., within the dimensions of the pocket 64 defined by the first and second side edges 70, 72 and the upper and lower lateral edges 74, 76 of the pocket 64). This is due to the fact that the inner longitudinal edge 96a of each of the secondary first fastening components 96 is disposed laterally inside of the respective side edges 70, 72 of the pocket 64. This configuration as depicted in FIG. 7 may be necessary where the width 78 of the pocket 64 is large in respect to the lateral width of the strip 89, which may occur in smaller sized diapers, and can result in the side edges 70, 72 of the pocket 64 to overlap with the respective inner longitudinal edges 96a of the secondary first fastening components 96. While not as desirable as the configurations of FIGS. 4-6 where the inner longitudinal edge 96a is laterally outside of the respective side edges 70, 72 of the pocket 64 for the reasons noted above, the embodiment depicted in FIG. 7 still provides some of the benefits noted above with respect to the secondary first fastening components 96 remaining stationary with respect to the absorbent assembly 44. For example, because at least a majority of the area of each of the secondary first fastening components 96 is outside of the pocket 64, that majority of the area of the secondary first fastening components 96 can remain stationary with respect to the absorbent assembly 44, even if the primary fastening system 82 moves with respect to its initial tension and/or fit.

Waist Elastic Members:

In an embodiment, the absorbent article 10 can have one or more waist elastic members, such as rear waist elastic member 52, which can be formed of any suitable elastic material. The rear waist elastic member 52 can be in a rear waist region 14 of the absorbent article 10. Suitable elastic materials for waist elastic members can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic member 52 can be omitted from the absorbent article 10 without departing from the scope of this disclosure.

EMBODIMENTS

Embodiment 1

An absorbent article including a front waist region including a front waist edge, a rear waist region including a rear waist edge, and a crotch region, the absorbent article further including a longitudinal axis and a lateral axis, the longitudinal axis providing a first longitudinal half of the absorbent article and a second longitudinal half of the absorbent article, the absorbent article being configured to move between an unfastened condition and a fastened condition, the absorbent article comprising: an absorbent assembly including a bodyside liner, an outer cover, and an absorbent body disposed between the bodyside liner and the outer cover; a fastening system including a primary fastening system and a secondary fastening system, the primary fastening system including at least one primary first fastening component in the rear waist region and at least one primary second fastening component in the front waist region, the secondary fastening system including a first secondary first fastening component in the front waist region and at least one secondary second fastening component in the rear waist region, the first secondary first fastening component including a first inner longitudinal edge and a first outer longitudinal edge; and a pocket including a first side edge, a second side edge opposite from the first side edge, an upper lateral edge, and a lower lateral edge, the pocket being closed with respect to the absorbent assembly at least at the first side edge and the second side edge and being open with respect to the absorbent assembly at least at the lower lateral edge, the pocket being disposed in the front waist region such that the at least one primary first fastening component is configured to engage the pocket when engaging the at least one primary second fastening component in the fastened condition of the absorbent article and the first secondary first fastening component engaging the at least one secondary second fastening component in the fastened condition.

Embodiment 2

An absorbent article including a front waist region including a front waist edge, a rear waist region including a rear waist edge, and a crotch region, the absorbent article further including a longitudinal axis and a lateral axis, the longitudinal axis providing a first longitudinal half of the absorbent article and a second longitudinal half of the absorbent article, the absorbent article comprising: an absorbent assembly including a bodyside liner, an outer cover, and an absorbent body disposed between the bodyside liner and the outer cover; a pocket disposed in the front waist region, the pocket including a first side edge, a second side edge opposite from the first side edge, an upper lateral edge, and a lower lateral edge, the pocket being closed with respect to the absorbent assembly at least at the first side edge and the second side edge and being open with respect to the absorbent assembly at least at the lower lateral edge; and a fastening system including a primary fastening system and a secondary fastening system, the primary fastening system including at least one primary first fastening component in the rear waist region and at least one primary second fastening component in the front waist region, the secondary fastening system including a first secondary first fastening component in the front waist region and at least one secondary second fastening component in the rear waist region, the first secondary first fastening component being disposed in the first longitudinal half of the absorbent article, the first secondary first fastening component including a first inner longitudinal edge, at least a portion of the first inner longitudinal edge being laterally outside of the first side edge of the pocket.

Embodiment 3

An absorbent article including a front waist region including a front waist edge, a rear waist region including a rear waist edge, and a crotch region, the absorbent article further including a longitudinal axis and a lateral axis, the longitudinal axis providing a first longitudinal half of the absorbent article and a second longitudinal half of the absorbent article, the absorbent article comprising: an absorbent assembly including a bodyside liner, an outer cover, and an absorbent body disposed between the bodyside liner and the outer cover; a pocket disposed in the front waist region, the pocket including a first side edge, a second side edge opposite from the first side edge, an upper lateral edge, and a lower lateral edge, the pocket being closed with respect to the absorbent assembly at least at the first side edge and the second side edge and being open with respect to the absorbent assembly at least at the lower lateral edge; and a fastening system including a primary fastening system and a secondary fastening system, the primary fastening system including at least one primary first fastening component in the rear waist region and at least one primary second fastening component in the front waist region, the secondary fastening system including a first secondary first fastening component in the front waist region and at least one secondary second fastening component in the rear waist region, the first secondary first fastening component being disposed in the first longitudinal half of the absorbent article, the first secondary first fastening component comprising a first inner longitudinal edge, a first outer longitudinal edge and a first area, a majority of the first area being outside of the pocket.

Embodiment 4

An absorbent article including a front waist region including a front waist edge, a rear waist region including a rear waist edge, and a crotch region, the absorbent article further including a longitudinal axis and a lateral axis, the longitudinal axis providing a first longitudinal half of the absorbent article and a second longitudinal half of the absorbent article, the absorbent article comprising: an absorbent assembly including a bodyside liner, an outer cover, and an absorbent body disposed between the bodyside liner and the outer cover, the absorbent assembly further including a first longitudinal edge and a second longitudinal edge, the first longitudinal edge connecting the front waist edge and the rear waist edge and being disposed in the first longitudinal half of the absorbent article and the second longitudinal edge connecting the front waist edge and the rear waist edge and being disposed in the second longitudinal half of the absorbent article; a pocket disposed in the front waist region, the pocket including a first side edge, a second side edge opposite from the first side edge, an upper lateral edge, and a lower lateral edge, the pocket being closed with respect to the absorbent assembly at least at the first side edge and the second side edge and being open with respect to the absorbent assembly at least at the lower lateral edge; and a fastening system including a primary fastening system and a secondary fastening system, the primary fastening system including at least one primary first fastening component in the rear waist region and at least one primary second fastening component in the front waist region, the secondary fastening system including a first secondary first fastening component in the front waist region and at least one secondary second fastening component in the rear waist region, the first secondary first fastening component being disposed in the first longitudinal half of the absorbent article and including a first inner longitudinal edge and a first outer longitudinal edge, the first inner longitudinal edge of the first secondary first fastening component being laterally closer to the first longitudinal edge of the absorbent assembly than the first side edge of the pocket is to the first longitudinal edge of the absorbent assembly.

Embodiment 5

The absorbent article of embodiment 3, wherein the majority of the first area is laterally outside of the first side edge of the pocket.

Embodiment 6

The absorbent article of any one of embodiments 1-4, wherein the primary fastening system includes a pair of primary first fastening components, and wherein the secondary fastening system includes a pair of secondary first fastening components and a pair of secondary second fastening components, the pair of secondary first fastening components including the first secondary first fastening component and a second secondary first fastening component, the second secondary first fastening component being disposed in the second longitudinal half of the absorbent article.

Embodiment 7

The absorbent article of embodiment 6, wherein the second secondary first fastening component includes a second inner longitudinal edge, at least a portion of the second inner longitudinal edge being laterally outside of the second side edge of the pocket.

Embodiment 8

The absorbent article of embodiment 7, wherein an entire length of the first inner longitudinal edge of the first secondary first fastening component is laterally outside of the first side edge of the pocket and an entire length of the second inner longitudinal edge of the second secondary first fastening component is laterally outside of the second side edge of the pocket.

Embodiment 9

The absorbent article of any one of embodiments 6-8, wherein the second secondary first fastening component comprises a second area, a majority of the second area being laterally outside of the second side edge of the pocket.

Embodiment 10

The absorbent article of any one of embodiments 6-9, wherein the second secondary first fastening component includes a second inner longitudinal edge, the second inner longitudinal edge of the second secondary first fastening component being laterally closer to the second longitudinal edge of the absorbent assembly than the second side edge of the pocket is to the second longitudinal edge of the absorbent assembly.

Embodiment 11

The absorbent article of any one of the preceding embodiments, wherein a material forms at least a portion of the at least one primary second fastening component, and wherein at least a portion of the material forms at least a portion of the pocket.

Embodiment 12

The absorbent article of embodiment 11, wherein the first secondary first fastening component is disposed on the material.

Embodiment 13

The absorbent article of embodiment 12, wherein the secondary fastening system further comprises a second secondary first fastening component disposed in the second longitudinal half of the absorbent article, the second secondary first fastening component including a second inner longitudinal edge, the second secondary first fastening component being disposed on the material, and wherein at least a portion of the second inner longitudinal edge is laterally outside of the second side edge of the pocket.

Embodiment 14

The absorbent article of embodiment 10, wherein the first secondary first fastening component is disposed on a first carrier material.

Embodiment 15

The absorbent article of embodiment 14, wherein the secondary fastening system further comprises a second secondary first fastening component disposed in the second longitudinal half of the absorbent article, and wherein the second secondary first fastening component is disposed on a second carrier material.

Embodiment 16

The absorbent article of embodiment 15, wherein the second secondary first fastening component includes a second inner longitudinal edge, and wherein at least a portion of the second inner longitudinal edge is laterally outside of the second side edge of the pocket.

Embodiment 17

The absorbent article of embodiment 15 or 16, wherein the first carrier material is directly coupled to the material and the second carrier material is directly coupled to the material.

Embodiment 18

The absorbent article of embodiment 15 or 16, wherein the first carrier material includes a first innermost edge and the second carrier material includes a second innermost edge, wherein the material includes a first side edge and a second side edge, and wherein the first carrier material and the second carrier material are coupled directly to the outer cover such that the first innermost edge of the first carrier material is disposed laterally outside of the first side edge of the material and the second innermost edge of the second carrier material is disposed laterally outside of the second side edge of the material.

Embodiment 19

The absorbent article of any one of the preceding embodiments, wherein the pocket is further closed with respect to the absorbent assembly at the upper lateral edge.

Embodiment 20

The absorbent article of any one of embodiments 6-10 or 12-18, wherein the pair of primary first fastening components and the pair of secondary first fastening components each comprise a hook material, and wherein the at least one primary second fastening component and the pair of secondary second fastening components each comprise a loop material.

Embodiment 21

The absorbent article of any one of embodiments 6-10 or 12-20, wherein the first secondary first fastening component and the second secondary first fastening component are each substantially rectangular in shape.

Embodiment 22

The absorbent article of any one of preceding embodiments, wherein the first secondary first fastening component further includes a bottom edge, the first secondary first fastening component being disposed such that the bottom edge is closer to the front waist edge than the lower lateral edge of the pocket is to the front waist edge.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article including a front waist region including a front waist edge, a rear waist region including a rear waist edge, and a crotch region, the absorbent article further including a longitudinal axis and a lateral axis, the longitudinal axis providing a first longitudinal half of the absorbent article and a second longitudinal half of the absorbent article, the absorbent article being configured to move between an unfastened condition and a fastened condition, the absorbent article comprising:
   an absorbent assembly including a bodyside liner, an outer cover, and an absorbent body disposed between the bodyside liner and the outer cover;
   a fastening system including a primary fastening system and a secondary fastening system, the primary fastening system including a pair of primary first fastening components in the rear waist region and at least one primary second fastening component in the front waist region, the secondary fastening system including a pair of secondary first fastening components including a first secondary first fastening component and a second secondary first fastening component in the front waist region and a pair of secondary second fastening components in the rear waist region, the first secondary first fastening component including a first inner longitudinal edge and a first outer longitudinal edge and the second secondary first fastening component being disposed in the second longitudinal half of the absorbent article; and
   a pocket including a first side edge, a second side edge opposite from the first side edge, an upper lateral edge, and a lower lateral edge, the pocket being closed with respect to the absorbent assembly at least at the first side edge and the second side edge and being open with respect to the absorbent assembly at least at the lower lateral edge, the pocket being disposed in the front waist region such that the at least one primary first fastening component is configured to engage the pocket when engaging the at least one primary second fastening component in the fastened condition of the absorbent article and the first secondary first fastening component engaging the at least one secondary second fastening component in the fastened condition.

2. The absorbent article of claim 1, wherein the second secondary first fastening component includes a second inner longitudinal edge, at least a portion of the second inner longitudinal edge being laterally outside of the second side edge of the pocket.

3. The absorbent article of claim 2, wherein an entire length of the first inner longitudinal edge of the first secondary first fastening component is laterally outside of the first side edge of the pocket and an entire length of the second inner longitudinal edge of the second secondary first fastening component is laterally outside of the second side edge of the pocket.

4. The absorbent article of claim 1, wherein the second secondary first fastening component comprises a second area, a majority of the second area being laterally outside of the second side edge of the pocket.

5. The absorbent article of claim 1, wherein the second secondary first fastening component includes a second inner longitudinal edge, the second inner longitudinal edge of the second secondary first fastening component being laterally closer to the second longitudinal edge of the absorbent assembly than the second side edge of the pocket is to the second longitudinal edge of the absorbent assembly.

6. The absorbent article of claim 5, wherein the first secondary first fastening component is disposed on a first carrier material.

7. The absorbent article of claim 6, wherein the secondary fastening system further comprises a second secondary first fastening component disposed in the second longitudinal half of the absorbent article, and wherein the second secondary first fastening component is disposed on a second carrier material.

8. The absorbent article of claim 7, wherein the second secondary first fastening component includes a second inner longitudinal edge, and wherein at least a portion of the second inner longitudinal edge is laterally outside of the second side edge of the pocket.

9. The absorbent article of claim 7, wherein the first carrier material is directly coupled to the material and the second carrier material is directly coupled to the material.

10. The absorbent article of claim 7, wherein the first carrier material includes a first innermost edge and the second carrier material includes a second innermost edge, wherein the material includes a first side edge and a second side edge, and wherein the first carrier material and the second carrier material are coupled directly to the outer cover such that the first innermost edge of the first carrier material is disposed laterally outside of the first side edge of the material and the second innermost edge of the second carrier material is disposed laterally outside of the second side edge of the material.

11. The absorbent article of claim 1, wherein the pair of primary first fastening components and the pair of secondary first fastening components each comprise a hook material, and wherein the at least one primary second fastening component and the pair of secondary second fastening components each comprise a loop material.

12. The absorbent article of claim 1, wherein the first secondary first fastening component and the second secondary first fastening component are each substantially rectangular in shape.

13. The absorbent article of claim 1, wherein the first secondary first fastening component further includes a bottom edge, the first secondary first fastening component being disposed such that the bottom edge is closer to the front waist edge than the lower lateral edge of the pocket is to the front waist edge.

14. An absorbent article including a front waist region including a front waist edge, a rear waist region including a rear waist edge, and a crotch region, the absorbent article further including a longitudinal axis and a lateral axis, the longitudinal axis providing a first longitudinal half of the absorbent article and a second longitudinal half of the absorbent article, the absorbent article comprising:
  an absorbent assembly including a bodyside liner, an outer cover, and an absorbent body disposed between the bodyside liner and the outer cover;
  a pocket disposed in the front waist region, the pocket including a first side edge, a second side edge opposite from the first side edge, an upper lateral edge, and a lower lateral edge, the pocket being closed with respect to the absorbent assembly at least at the first side edge and the second side edge and being open with respect to the absorbent assembly at least at the lower lateral edge; and
  a fastening system including a primary fastening system and a secondary fastening system, the primary fastening system including at least one primary first fastening component in the rear waist region and at least one primary second fastening component in the front waist region, the secondary fastening system including a first secondary first fastening component and a second secondary first fastening component in the front waist region and at least one secondary second fastening component in the rear waist region, the first secondary first fastening component being disposed in the first longitudinal half of the absorbent article and the second secondary first fastening component being disposed in the second longitudinal half of the absorbent article, the first secondary first fastening component including a first inner longitudinal edge, at least a portion of the first inner longitudinal edge being laterally outside of the first side edge of the pocket, the second secondary first fastening component including a second inner longitudinal edge, at least a portion of the second inner longitudinal edge being laterally outside of the second side edge of the pocket,
  wherein a material forms at least a portion of the at least one primary second fastening component, and wherein at least a portion of the material forms at least a portion of the pocket, and
  wherein the first secondary first fastening component and the second secondary first fastening component are disposed on the material.

15. The absorbent article of claim 14, wherein the pocket is further closed with respect to the absorbent assembly at the upper lateral edge.

16. An absorbent article including a front waist region including a front waist edge, a rear waist region including a rear waist edge, and a crotch region, the absorbent article further including a longitudinal axis and a lateral axis, the longitudinal axis providing a first longitudinal half of the absorbent article and a second longitudinal half of the absorbent article, the absorbent article comprising:
  an absorbent assembly including a bodyside liner, an outer cover, and an absorbent body disposed between the bodyside liner and the outer cover;
  a pocket disposed in the front waist region, the pocket including a first side edge, a second side edge opposite from the first side edge, an upper lateral edge, and a lower lateral edge, the pocket being closed with respect to the absorbent assembly at least at the first side edge and the second side edge and being open with respect to the absorbent assembly at least at the lower lateral edge; and
  a fastening system including a primary fastening system and a secondary fastening system, the primary fastening system including at least one primary first fastening component in the rear waist region and at least one primary second fastening component in the front waist region, the secondary fastening system including a first secondary first fastening component in the front waist region and at least one secondary second fastening component in the rear waist region, the first secondary first fastening component being disposed in the first longitudinal half of the absorbent article, the first secondary first fastening component comprising a first inner longitudinal edge, a first outer longitudinal edge and a first area, a majority of the first area being outside of the pocket, wherein
  wherein a material forms at least a portion of the at least one primary second fastening component, and wherein at least a portion of the material forms at least a portion of the pocket, and wherein the first secondary first fastening component is disposed on the material.

17. The absorbent article of claim 16, wherein the majority of the first area is laterally outside of the first side edge of the pocket.

\* \* \* \* \*